United States Patent [19]

Shibata et al.

[11] Patent Number: 5,288,610
[45] Date of Patent: Feb. 22, 1994

[54] DETECTING REAGENT FOR ANTIPLATELET ANTIBODY

[75] Inventors: Yoichi Shibata, Tokyo; Naohiro Ozawa, Yono, both of Japan

[73] Assignee: Olympus Optical Co., Ltd., Tokyo, Japan

[21] Appl. No.: 508,922

[22] Filed: Apr. 12, 1990

[30] Foreign Application Priority Data

May 16, 1989 [JP] Japan .................. 1-122392

[51] Int. Cl.$^5$ ................ G01N 33/543; G01N 33/544; G01N 33/546; G01N 33/555
[52] U.S. Cl. .................. 435/7.21; 435/7.24; 435/961; 436/578; 436/520; 436/528; 436/533; 436/534; 436/543; 436/829
[58] Field of Search ............ 435/7.24, 961, 7.21; 436/506, 518, 520, 543, 533, 534, 528, 829

[56] References Cited

U.S. PATENT DOCUMENTS

| 4,959,308 | 9/1990 | Ogden | 435/7 |
| 5,110,726 | 5/1992 | Ogden | 435/7.21 |

OTHER PUBLICATIONS

I. M. Roitt, *Essential Immunology*, 5th Edition, Blackwell Scientific Publications, Oxford, UK, 1984, pp. 159–161.

W. J. Herbert, in D. M. Weir (Ed.), *Handbook of Experimental Immunology*, Third Edition, Blackwell Scientific Publications, Oxford, 1978, Chapter 20.

*Primary Examiner*—David Saunders
*Attorney, Agent, or Firm*—Frishauf, Holtz, Goodman & Woodward

[57] ABSTRACT

A detecting reagent for an antiplatelet antibody, comprises a carrier particle, and a platelet antigen component immobilized on a surface of the carrier particle. The reagent particles do not agglutinate with each other, contrary to the platelets subjected to natural agglutination, probably because the platelet membrane antigen component immobilized on the carrier particle is solubilized in advance.

9 Claims, No Drawings

DETECTING REAGENT FOR ANTIPLATELET ANTIBODY

BACKGROUND OF THE INVENTION

1. Field of the Invention

The present invention relates to a detecting reagent for an antiplatelet antibody. This detecting reagent is used to detect an antiplatelet antibody present in a blood of a patient at the time of, e.g., platelet transfusion.

2. Description of the Related Art

Platelets are akaryocites which are present in a blood and each of which has a diameter of 2 to 3 μm. The platelets are produced by fragmentation of megakaryocytes present in the bone marrow. When platelet in a blood are brought into contact with damaged hemangioendothelial cells, they agglutinate with each other and play an important role for hemostasis.

In recent years, a platelet transfusion therapy has been made to aim at hemostasis and hemorrhagic prevention for patients who have a hemorrhagic tendency caused by thrombocytopenia or thrombopathy. By this therapy, many lot of patients are saved from death caused by hemorrhage, and their lives can be saved or prolonged. The amount of a platelet preparation used has been abruptly increased, with development of platelet transfusion.

An antibody against the antigen present on a surface membrane of the transfused platelet is produced in case that a large amount of platelets must be frequently transfused over a long period of time. Examples of such case is the platelet transfusion therapy for patients who suffer from acute leukemia and asplastic anemia. When this occurs, platelets transfused from random donors cannot cause any desired response of the patients, and no increase in the number of platelets is found after platelet transfusion. When platelet transfusion does not function well due to the reason described above, platelets having an antigen type which does not react with an antiplatelet antibody of such a patient must be transfused to this patient.

Antiplatelet antibodies are classified into an alloantibody and an autoantibody.

The antiplatelet alloantibody is produced by the above-mentioned platelet transfusion or pregnancy. The isoantibody does not only influence an effect of platelet transfusion described above but also causes post-transfusion purpura and neonatal thrombocytopenic purpura.

On the other hand, the antiplatelet autoantibody is produced in a patient who suffers from an autoimmune disease such as idiopathic thrombocytopenic purpura. The autoantibody is deemed to be a substance which causes an autoimmune disease.

Various conventional methods are available to detect the antiplatelet antibody as follows:

(1) Agglutination Assay

This method is the first method developed to detect the antiplatelet antibody and is originally used to detect a $Pl^A$ antigen series and a Ko antigen series. According to this method, an IgM antibody is mainly detected, but an IgG antibody is rarely detected. This method tends to cause nonspecific agglutination caused by natural agglutination of platelets and has a low sensitivity.

(2) Complement-Fixation Reaction

After a sample serum, platelets, and a complement are reacted with each other, hemolysin labeled sheep blood cell are added to the reaction mixture, and an amount of consumption of the complement is determined from a degree of hemolysis of the hemolysin labeled sheep blood cell. This method can detect an HLA antigen on a surface membrane of the platelet and a blood group antigen of ABO type, but has a low sensitivity. In addition, it is difficult to detect the antiplatelet antibody if a sample serum has anticomplement activity.

(3) Antiglobuline Consumption Test

After platelets are reacted with an inactivated sample serum, the reaction mixture is washed. After an antiglobulin serum is added to the mixture, the mixture is subjected to a centrifugal operation. An anti-D antibody labeled blood cell is added to and reacted with the supernatant of the reaction mixture to detect an antiplatelet antibody in accordance with an antiglobulin titer of the supernatant. This method tends to cause pseudopositive determination and has a low sensitivity.

(4) RIA (Radioimmuneoassay)

The RIA is an antiglobulin test using an anti-human IgG labeled with a radioactive isotope. The isotope-labeled anti-human IgG is coupled to an antiplatelet antibody of a platelet of a patient, and the radioactive isotope elements coupled to the platelets are counted.

(5) MPHA (Mixed passive haemagglutination)

Platelets of solid phase are formed on the well wall of a U-shaped microplate, and a sample serum is added to and reacted with the platelets. After the well is washed, anti-human IgG labeled sheep red cell is added to the reaction mixture and is reacted with it. An agglutination pattern in which the sheep red cells collect in a central portion of the well is determined to be negative, and an agglutination pattern in which sheep red cells are scattered on the entire area is determined to be positive, thereby detecting a platelet antibody.

Of the conventional methods described above, the agglutination assay (1) requires only one step for the entire reaction and has simple test procedures. The agglutination assay, however, has disadvantages in that the IgG class antibodies cannot be detected and nonspecific agglutination tends to occur. Therefore, the agglutination assay is not suitable for practical applications.

Other conventional methods, i.e., the complement-fixation reaction (2) to the MPHA (5) require two or more steps each in the measurement. Therefore, the measurement time is prolonged, and the measuring operations are complicated.

SUMMARY OF THE INVENTION

The present invention has been made in consideration of the above problems, and has as its object to provide a detecting reagent for an antiplatelet antibody, which can detect an antiplatelet antibody with a passive haemagglutination reaction in one step.

In order to achieve the above object, there is provided a detecting reagent for an antiplatelet antibody, comprising:
 a carrier particle; and
 a platelet antigen component immobilized on a surface of the carrier particle.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

The present inventor made extensive studies to develop a simple method of measuring an antiplatelet antibody within a short period of time and was successful in detection of an antiplatelet antibody in a sample serum by a passive haemagglutination reaction in one step upon mixing of the sample serum with a carrier particle on which an antigen component of the platelet is immobilized.

The antigen component of the platelet can be obtained as a solubilized lysate upon application of a physical force such as an ultrasonic force to a platelet. The antigen component ca also be obtained by solubilizing the platelet upon a treatment of the platelet with a surfactant. Alternatively, a physical force is applied to the platelet to crush it, and the crushed platelet pieces are treated with a surfactant to solubilize the platelet, thereby obtaining the antigen component.

The carrier particle used in the present invention may be any particle which can be used in the passive agglutination reaction. Examples of the carrier particle are a red cell of man or an animal (e.g, sheep or chicken), a liposome, a latex particle, and a gelatin particle.

A known method can be used as a method of immobilizing an antigen component of a platelet on a carrier particle, and is exemplified by a method using a coupling agent such as tannic acid, glutaraldehyde, carbodiimide, or chromium chloride. When a glass particle is used as the carrier particle, its coupling agent is N-$\beta$-(aminoethyl)-$\gamma$-aminopropyl-trimethyoxysilane. The antigen component may be immobilized on the carrier particle by physical adsorption without using any coupling agent.

In the detecting reagent for antiplatelet antibody according to the present invention, particles of the reagent do not agglutinate with each other, contrary to the platelets subjected to natural agglutination, propably because the platelet membrane antigen component immobilized on the carrier particle is solubilized in advance. Therefore, a good measurement result with good reproducibility can be obtained without causing natural agglutination between the particles.

In addition, detection by passive haemagglutination reaction of one step is possible because the antigen is immobilized directly on the carrier particle.

The present invention will be described in detail by way of its example. As is apparent from the detailed description of the example, an antiplatelet antibody can be detected by a passive haemagglutination reaction in one step.

EXAMPLE 1

Preparation of Anti-platelet Antigen Component

I. Typing of Platelet

Prior to solubilization of a platelet, its platelet-specific antigen was identified by the following procedures.

A human whole blood of type O was collected at a volume ratio of 7:1 with respect to an ACD-A solution (available from Terumo Corp.), and the whole blood added with the ACD-A solution was subjected to centrifugal separation at a speed of 1,400 rpm for 10 minutes, thereby separating a platelet-rich plasma (PRP). In order to increase a yield of the platelets, an ACD-A solution was added to the resultant PRP in an amount of 10% by volume of the PRP, and the resultant mixture was subjected to centrifugal separation at a speed of 2,500 rpm for 15 minutes. The supernatant was removed, and a platelet concentrate (P.C.) was obtained. This platelet concentrate was washed with a physiological saline, and finally a platelet suspension solution (about $1 \times 10^5$ platelets/$\mu$l) was obtained.

The resultant platelet suspension solution was dropped in an amount of 5 $\mu$l on each well of a styrol microplate (Terasaki Plate U Type (available from Robins Corp.)) electrostatically discharged in advance. The microplate was placed on a plate mixer to stir the solution in each well for 10 seconds. The microplate was then set in a plate centrifugal separator, and the solution in each well was centrifugally separated at 2,000 rpm for 5 minutes, so that the platelets were coated on to the bottom surface of each well.

A fixing solution was prepared by diluting a 35% formalin solution to five times with a PBS (phosphate buffered saline), and adjusting a pH value to 7.2 with addition of NaOH. The fixing solution thus obtained was added to each well by 10 l/well and was left to stand for 20 minutes. After each well was washed with a physiological saline three times, it was confirmed with naked eyes that a single layer of platelets was formed on the bottom surface of each well. Preparation of typing microplates were thus completed.

Various serums were added by 5 $\mu$l/well to the wells of the microplate to which the platelets were immobilized and were reacted with the platelets at room temperature for an hour. After the reaction, each well was washed five times with a PBS having a pH of 7.2 and containing a 0.05% Tween 20. A 0.2% suspension of an anti-human IgG labeled seep sheep red cell was added by 5 $\mu$l/well to the wells, and the mixtures were left to stand at room temperature for 3 hours, and agglutination patterns were then determined. Determination results are shown in Table 1. A positive sample is represented by +, and a negative sample is represented by — in Table 1.

In actual typing, five types of platelets obtained from five donors were used. Antiserums used in Example 1 were human anti-serums (e.g., anti-Pl$^{A1}$ anti-Pl$^{A2}$ anti-Yuk$^a$, anti-Yuk$^b$, anti-Bak$^a$, anti-Nak$^a$, anti-Sib$^a$, anti-Ko$^b$, and anti-Br$^a$) against platelet-specific antigens, and an anti-serums (e.b., anti-HLA) against an HLA antigen.

TABLE 1

| Donor No. | Anti-Serum | | | | |
|---|---|---|---|---|---|
| | Anti-Pl$^{A1}$ | Anti-Pl$^{A2}$ | Anti-Yuk$^a$ | Anti-Yuk$^b$ | Anti-Bak$^a$ |
| 1 | + | — | — | + | + |
| 2 | + | — | — | + | + |
| 3 | + | — | — | + | + |
| 4 | + | — | — | + | — |
| 5 | — | — | — | — | — |

| Donor No. | Anti-Serum | | | | |
|---|---|---|---|---|---|
| | Anti-Nak$^a$ | Anti-Sib$^a$ | Anti-Ko$^a$ | Anti-Br$^a$ | Anti-HLA |
| 1 | + | + | + | — | — |
| 2 | + | — | — | — | — |
| 3 | — | — | — | — | — |
| 4 | — | — | — | — | — |
| 5 | — | — | — | — | — |

II. Solubilization of Platelets

In the MPHA method, the platelets of donor No. 1 which were positive for the anti-P1$^{A1}$, anti-Yuk$^b$, anti-Bak$^a$, anti-Nak$^a$, anti-Sib$^a$, and anti-Ko$^a$ were solubilized by the following procedures.

0.8% chloroquine was added to a platelet suspension solution (105/µl) and was reacted with it at room temperature for an hour. The reacted platelets were washed with a physiological saline twice, and 2.5-ml platelets were crushed with sonic oscillation by a Sonica-tor (available from Tomy Corp.) for 20 seconds. $10^5$ G of the crushed platelets were centrifugally separated for 30 minutes and washed once. 1% Triton X-100 was added to the separated platelets. The platelets were further centrifugally separated at $10^5$ G for 30 minutes, and the platelet membrane fraction in the supernatant was sampled to obtain a solubilized platelet membrane antigen.

In the above treatment the HLA antigen was removed by the chloroquine treatment. The chloroquine treatment however, can be omitted to cause both the platelet specific antigen and the HLA antigen to exist in the finally obtained platelet membrane antigen fraction.

PREPARATION OF CARRIER PARTICLE

Fresh sheep red cells within two days after the collection were washed with a PBS four times. The PBS was added to a pellet of the washed red cells to prepare a 5% red cell suspension. 20 ml of 2.5% glutaraldehyde solution were added to the 100 ml of the red cell suspension and were shaken and reacted with it at room temperature for 3 hours. The sheep red cells to which a carbonyl group was introduced was washed with a PBS four times to add the PBS, thereby obtaining a 5% suspension.

IMMOBILIZATION OF PLATELET ANTIGEN COMPONENT ON CARRIER PARTICLE 100 ml of a 0.02% tannic acid solution were added to 100 ml of the 5% suspension of the sheep red cells treated as described above and were reacted with it at 37° C. for 15 minutes. The resultant mixture was then washed with a PBS once. 100 ml of the 5% suspension of the sheep red cells treated with tannic acid as described above were added to 100 ml of the solubilized platelet membrane antigen solution (10 µg/ml) prepared as described above and were reacted with it under stirring at room temperature for 2 hours. By this reaction, the solubilized platelet membrane antigen was immobilized on the surface of the sheep red cell. When the immobilization reaction was completed, the treated sheep red cells were washed four times, and a 3% normal rabbit serum (NRS) was added thereto to prepare a 2% blood cell suspension solution.

DETECTION OF ANTIPLATELET ANTIBODY

The platelet membrane antigen labeled sheep red cell (to be referred to as an indicator cell hereinafter) was used to perform an agglutination reaction with the antiplatelet antibody in accordance with the following procedures.

A PBS (pH: 7.2) was added to the first to third wells of a U-shaped microplate by 25 µl/well. 25 µl of a sample serum were poured in the first well and were stirred well (dilution: twice). Similarly, serum samples diluted four times and eight times were respectively dispensed into the second and third wells, respectively. Serum samples diluted $2^n$ times were sequentially dispensed in the fourth and subsequent wells. The indicator cells were added to each well by 25 µl/well, and were stirred well. The lid of each cell was then closed, and each mixture was left to stand at room temperature for 2 hours. Agglutination patterns formed on the bottoms of the wells were determined.

Sample serums were a human serum of a healthy man, an anti-P1$^{A1}$ serum, an anti-Yuk$^b$ serum, an anti-Bak$^a$ serum, an anti-Nak$^a$ serum, an anti-Sib$^a$ serum, an anti-Ko$^a$ serum, and an anti-HLA serum.

The reaction with the serum of the healthy man exhibited a pseudopositive up to a dilution ratio of 1:4, but were negative when the dilution ratio was 1:8 or more.

The reaction with the anti-P1$^{A1}$ antibody having a higher titer was negative.

The P1$^{A1}$ and anti-Yuk$^b$ antibodies could be detected with a sensitivity equivalent to that in the MPHA method.

The Nak$^a$ antibody could be detected although the reaction was rather weak.

Other antibodies, i.e., anti-Bak$^a$, anti-Sib$^a$, and anti-Ko$^a$ antibodies could not be detected.

As is apparent from the above description, the indicator cell obtained in the above example reacts with the anti-P1$^{A1}$ anti-Yuk$^b$, and anti-Nak$^a$ antibodies, but does not react with the anti-Bak$^a$, anti-Sib$^a$, and anti-Ko$^a$ antibodies. Therefore, the present invention is effective for identifying patients who possess antibodies against the anti-P1$^{A1}$, anti-Yuk$^b$, and anti-Nak$^a$ antibodies. The indicator cell of this example may be combined with an indicator cell having another specificity to effectively perform screening of patients who possess antiplatelet antibodies and typing of antiplatelet antibodies.

Since the solubilized platelet membrane antigen is used in the indicator cell of this example, nonspecific agglutination between the indicator cells does no occur, thereby achieving good reproducibility.

Additional advantages and modifications will readily occur to those skilled in the art. Therefore, the invention in its broader aspects is not limited to the specific details, and illustrated examples shown and described herein. Accordingly, various modifications may by without departing from the spirit or scope of the general inventive concept as defined by the appended claims and their equivalents.

What is claimed is:

1. A detecting reagent for an antiplatelet antibody, said detecting reagent comprising a carrier particle coupled to a solubilized lysate of a platelet from a human, said solubilized lysate being obtained by treating said platelet by sonication so as to extract alloantigens from among platelet antigens, said alloantigens being immobilized on the carrier particle by passive adsorption onto the carrier particle, said carrier particle agglutinates with anti-P1$^{A1}$, anti-Yuk$^b$ and anti-Nak$^a$ antibody, but does not agglutinate with anti-Bak$^a$, anti-Sib$^a$ and anti-Ko$^a$ antibodies.

2. The detecting reagent according to claim 1, wherein said solubilized lysate of a platelet is a precipitate obtained by treating said platelet with an ultrasonic wave, followed by centrifugal separation.

3. The detecting reagent according to claim 1, wherein the carrier is an erythrocyte of an animal.

4. The detecting reagent according to claim 1, wherein the carrier is selected from the group consisting of a liposome, a latex and gelatin.

5. The detecting reagent according to claim 1, wherein said passive adsorption is carried out by contact with tannic acid.

6. The detecting reagent according to claim 5, wherein the carrier particle is an erythrocyte from a sheep.

7. A method of detecting an antiplatelet antibody by a passive agglutination reaction comprising:

combining a serum sample from a patient with a detecting reagent comprising a carrier particle coupled to a solubilized lysate of a platelet from a human, the solubilized lysate being obtained by treating said platelet by sonication so as to extract alloantigens from among platelet antigens, said alloantigens being immobilized on the carrier particle by passive adsorption onto the carrier particle, said carrier particle agglutinates with anti-$Pl^{Al}$, anti-$Yuk^b$ and anti-$Nak^a$ antibody, but does not agglutinate with anti-$Bak^a$, anti-$Sib^a$ and anti-$Ko^a$ antibodies; and detecting the presence of antiplatelet antibody by carrying out an agglutination reaction.

8. The method according to claim 7, wherein the carrier is selected from the group consisting of an erythrocyte, a liposome, latex and gelatin.

9. The method according to claim 7, wherein said passive adsorption is carried out by contact with tannic acid.

* * * * *